United States Patent

Mletzko

(10) Patent No.: US 9,821,168 B2
(45) Date of Patent: Nov. 21, 2017

(54) MEDICAL BIOELECTRIC PLASMA BEAM

(71) Applicant: Hardy Mletzko, El Paso, TX (US)

(72) Inventor: Hardy Mletzko, El Paso, TX (US)

(73) Assignee: LUMIGENCE LLC, South Lake Tahoe, CA (US)

( * ) Notice: Subject to any disclaimer, the term of this patent is extended or adjusted under 35 U.S.C. 154(b) by 0 days.

(21) Appl. No.: 15/161,031

(22) Filed: May 20, 2016

(65) Prior Publication Data

US 2016/0339261 A1    Nov. 24, 2016

Related U.S. Application Data

(60) Provisional application No. 62/165,154, filed on May 21, 2015.

(51) Int. Cl.
*B23K 10/00* (2006.01)
*A61N 1/44* (2006.01)
*H05H 1/46* (2006.01)

(52) U.S. Cl.
CPC .............. *A61N 1/44* (2013.01); *H05H 1/46* (2013.01); *H05H 2001/4682* (2013.01); *H05H 2245/122* (2013.01)

(58) Field of Classification Search
CPC .... A61N 1/44; H05H 1/46; H05H 2001/4682; H05H 1/26
USPC ............ 219/121.48, 121.54, 121.51, 121.52
See application file for complete search history.

(56) References Cited

U.S. PATENT DOCUMENTS

| 775,869 A | 11/1904 | Strong | |
|---|---|---|---|
| 775,870 A | 11/1904 | Strong | |
| 2,011,743 A * | 8/1935 | Whitman | H01J 61/106 313/117 |
| 2,439,787 A * | 4/1948 | Atkins | H01J 65/046 315/244 |
| 2,786,181 A * | 3/1957 | Hamilton | G01R 27/2688 324/633 |

OTHER PUBLICATIONS

Sung, Fundamental approaches to the management of cardiac arrhythmias, 2000, p. 153, Springer, Netherlands.
Lockhart, Electrical Healing and the Violet Ray, www.arthurleej.com/Violet.pdf, 2009, p. 185, Arthur Lee Jacobson, Seattle, WA.
Strong, High Frequency Currents, 1908, p. 175, Rebman, New York.

(Continued)

*Primary Examiner* — Mark Paschall
(74) *Attorney, Agent, or Firm* — Gary L. Eastman, Esq.; Eastman & McCartney LLP

(57) ABSTRACT

Disclosed is a device having an oscillator and high voltage transformer connected to a glass-like tube filled with an inert gas or a mixture of inert gasses. The tube is located at the end of a wand having a handle. The output of the transformer is an RF high voltage signal. The output of the transformer is fed to the tube through a high voltage wire, where the signal excites the gas to produce a plasma-like beam. The tube is then applied to a patient's skin to aid in healing and the relief of additional ailments. The field generated by the tube interacts with the cells in the patient to increase transmembrane potential, stimulate ATP production, and inject negative ions and ozone into the surface of the user's skin to combat infection and disease.

16 Claims, 5 Drawing Sheets

(56) References Cited

OTHER PUBLICATIONS

Violet Ray, Wkipedia, en.wikipedia.org/wiki/Violet_ray.
Valone, Blomagnetic Healing, its History and a Rationale for its Use, Proceedings of the Whole Person Healing Conference, 2003, Integrity Research Institute, Washington, DC.
Tesla, High Frequency Oscillators for Electro-therapeutic and Other Purposes, The Electrical Engineer, Nov. 17, 1898, vol. XXVI, No. 550, pp. 477-481.

* cited by examiner

MEDICAL BIOELECTRIC PLASMA BEAM

RELATED APPLICATIONS

This application claims the benefit of priority to, and fully incorporates by this reference, the United States Provisional Patent Application for "Medical Bioelectric Plasma Beam", Ser. No. 62/165,154, filed on May 21, 2015.

FIELD OF THE INVENTION

The present invention pertains generally to medical equipment for use in patient treatment. More particularly, the present invention pertains to a medical device for use in bioelectric medicine, electrotherapy, electromagnetic medicine, bioelectromagnetic medicine, and light therapy. The Present invention is particularly, but not exclusively, useful as a medical device having multiple modes of operation to have effects in multiple medical disciplines.

BACKGROUND OF THE INVENTION

Bioelectromagnetics (BEMs) is the study of the effects of electromagnetic radiation upon biological systems and organisms. Radio frequency (RF) energy, in the form of radiating waves or electrical currents, has been used in medical treatments for over 75 years. Magnetic resonance imaging (MRI), and Ultrasound use RF for medical diagnostic imaging. Radiofrequency ablation (RFA), Ultrasound and Diathermy are all RF based treatments that are commonly used in modern medicine today.

The study of the effect of electromagnetic fields on biological systems have sometimes been associated with potential for harm to the body, however, there are many BEM instruments and devices re-emerging in the 21st century. These devices are based on high voltage Tesla coils, which apparently bring beneficial health improvements to human organisms. The Tesla coil class of therapy devices constitute pulsed electromagnetic fields (PEMF) that deliver broadband, wide spectrum, non-thermal photons and electrons deep into biological tissue. Electromedicine or electromagnetic healing are the terms applied to such developments in the ELF, RF, IR, visible, or UV band. With short term, non-contacting exposures of several minutes at a time, such high voltage Tesla PEMF devices may represent the ideal, noninvasive therapy of the future, accompanied by a surprising lack of harmful side effects. A biophysical rationale for the benefits of BEM healing a wide variety of illnesses, including cancer, proposes a correlation between a bioelectromagnetically restored transmembrane potential and the electron transport across cell membranes by electroporation. Electroporation, or electropermeabilization, is a molecular biology technique in which an electrical field is applied to cells in order to increase the permeability of the cell membrane, allowing chemicals, drugs, or DNA to be introduced into the cell.

Historically, as far back as 1890, the American Electro-Therapeutic Association conducted annual conferences on the therapeutic use of electricity and electrical devices by physicians on ailing patients. Some involved current flow through the patient, while others were electrically powered devices. Early on, medical doctors only utilized direct current (DC) devices when treating patients to relieve pain and treat "hysteria" in female patients.

In 1898, Nikola Tesla published a paper entitled, "High Frequency oscillators for Electro-Therapeutic and Other Purposes." In the paper, Tesla concluded that human tissue acts as an electrical "condenser" or capacitor. The "condenser" characteristic of the tissue allows large AC coils to be used to interact with the tissue without actually touching the tissue. For many years after Tesla published his paper, several medical professionals openly supported Tesla's conclusions.

Ongoing research in this field has established that high frequency electromagnetic fields can penetrate several centimeters into tissue, bone, and muscle where the application of the fields results in local hyperthermia. Research has also established that negative ions and traces of ozone have a wide range of health benefits, which includes boosting the immune system. High voltage Tesla-like devices produce an abundant amount of negative ions as well as traces of ozone. In conventional atmospheric/environmental ionizer applications, more than 95% of the produced negative ions are discharged to ground in precipitating out airborne particulates, leaving less than 5% for direct physiological therapeutic application.

Another important aspect of the effects of electromagnetic fields is their interaction with cellular transmembrane potential (TMP). Research has shown that damaged or diseased cells present an abnormally low TMP, approximately 80% lower than in healthy cells. The reduced TMP is indicative of reduced metabolism, impairment of the sodium-potassium pump activity, and reduced production of ATP. Literature dealing with the medical application of electromagnetic fields teaches that the level of TMP is proportional to the activity of the sodium-potassium pump, which creates a direct relationship to the rate of healing. According to research, healthy cells have TMP voltages of 70-90 millivolts. Due to the constant stresses of modern life and our environment, this cell voltage tends to drop as we age and get sick. As the voltage drops, the cell is unable to maintain a healthy environment. When a person is fatigued, cellular TMP drops to around 50 millivolts, where cancer cells have been shown to have a TMP of only 15 millivolts.

Research has shown that simple high voltage electrostatic fields can have many effects on the human body, most of which appear to be favorable. For example, high voltage fields were found to have a beneficial effect on mice as measured by their activity, rate of liver respiration, and ability to form antibodies. In contrast, mice deprived of any electrostatic fields by enclosing them in a Faraday cage showed opposite results.

Zeta-potential (ZP) is an electrostatic repulsive force that exists around atoms, molecules, dissolved gasses, proteinaceous fractions, particulates, organelles, blood corpuscles, and the surfaces of arterial, venous vessels, capillaries, and membranous/mucosal linings. ZP is the property that allows atoms and molecules to remain in suspension. ZP is also the property that allows a relatively frictionless, repulsive relation between the blood corpuscles and the vascular lining such that the heart is capable of pumping blood through miles of capillaries without excessive resistance. The existence of ZP is considered the basis of colloidal physical-chemistry and without which biological life would not be possible. A high ZP aids in: improved nutrition by nutrient sera suspension for better histological/cellular absorption; detoxification by toxin/waste product sera suspension for cellular, histological and systemic removal; enhancement/restoration of colloidal mineral suspension in lymph, blood stream, interbursal and intracellular sera, assisting in the reduction/prevention/reversal of depository diseases by decreasing sedimentation of serum ions, especially calcium ions which significantly increase plaque build-up in blood vessels by rendering oxidized cholesterol less soluble; disaggregation of RBCs in the "rouleau" condition in the blood stream, and; reduction of high blood pressure to normal levels by reducing blood viscosity (on the basis of repulsive forces produced by ZP interactions in the lining of arteries, arterioles, capillaries, blood corpuscles, and other circulating particulates in the blood stream that result in improved biophysical fluid dynamics that reduce frictional forces and the effects of other attractive forces.)

One of the most comprehensive and significant indicators for general disease states, including cancer, relates to the science of free radicals in the human body. Free radicals contain an odd number of electrons, which allows them to interact with another molecule to produce another free radical. A single free radical may go through 10,000 cycles of interacting with another molecule before the radical is terminated. Research has shown that many types of free radicals exist within our bodies and have been connected with the aging process. Research shows that application of a high voltage RF signal increases the amount of free electrons in a patient. The increased level of free electrons may combine with free radicals to decrease or eliminate the radical's effect on normal, healthy cells.

Radio frequency (RF) energy, in the form of radiating waves or electrical currents, has been used in medical treatments for over 75 years. Magnetic resonance imaging (MRI), and Ultrasound use RF energy for medical diagnostic imaging. RF ablation (RFA), Ultrasound, and Diathermy are all RF based treatments that are commonly used in modern medicine today. The present invention also utilizes RF but in a wholly different manner than the devices discussed above. The device generates a radio frequency that excites a mixture of inert gases and creates a plasma beam.

Plasma is a hot ionized gas consisting of approximately equal numbers of positively charged ions and negatively charged electrons. The presence of a non-negligible number of charge carriers makes plasma electrically conductive so that it responds strongly to electromagnetic fields. Plasma can be created by heating a gas or subjecting it to a strong electromagnetic field applied with a laser or Radio Frequency (RF) generator. The characteristics of plasmas are significantly different from those of ordinary neutral gases such that plasmas are considered a distinct "fourth state of matter."

Nikola Tesla conceptualized the use of high frequency electric currents for therapeutic use in the late 1800's. Tesla collaborated with Paul Oudin in Paris in 1892 who developed the first Violet Ray prototypes that debuted at the World's Columbian Exposition in 1893. Tesla met Frederick Strong in 1896 and collaborated on the first US built Violet Ray that Strong patented in 1904 (U.S. Pat. Nos. 775,869 and 775,870). Strong also developed the first glass vacuum electrode for the device in 1896. An embodiment of the present invention utilizes a modern version of the glass vacuum tube. The Violet Ray was commercially produced from early 1900's until 1951 and tens of thousands of units were produced and used to treat a variety of conditions in that time.

Various devices in the beauty industry employ a plasma-based design, which are used to tighten skin pores and treat acne. Most of these designs employ the effects of the high voltage stimulation of the tissue with the frequency being a negligible factor.

Plasma based lighting systems are also commonly used today, although they typically have little or no medical effects. These systems utilize a partially vacuumed glass tube filled with a pure noble or other gas mixture that is excited into a plasma state using high voltage or RF or a combination of both. Types of plasma-based lighting include fluorescent, neon, metal halide, cold cathode, and sodium vapor lamps.

For maximum effectiveness of a device, the output of the device should be at or close to the resonant frequency of the person receiving a treatment. Resonance is the condition of a system in which there is a sharp maximum probability for the absorption of electromagnetic radiation or capture of particles. Therefore, if a system is tuned to the resonant frequency of a person, the maximum amount of energy will be transferred from the device to the person. However, the resonant frequency of a person will shift when exposed to the output from a device. As the resonant frequency shifts, the effectiveness of the device decreases. To maintain the maximum effectiveness, the output frequency of the device should be adjusted to match the resonant frequency of the person.

What is needed in the industry is an electrical device capable of emitting a plasma-based beam for providing medical treatments. What is also needed is a device that senses the capacitance of the person receiving the treatment and adjusts its resonant output to match fluctuations in the capacitance of the person under treatment. Further, what is needed is a device that generates and emits negative ions and ozone such that a person using the device receives the beneficial effects of using the device.

SUMMARY OF THE INVENTION

The present invention uses RF but in a wholly different manner than other devices. The device generates a radio frequency (RF) that excites a mixture of inert gases and creates a plasma beam. The present invention consists of an enclosure containing a high voltage Radio Frequency oscillator circuit powered by 110 v or 220 v wall power. The high voltage RF output signal is sent via a 30 kV silicone wire to a cylinder shaped glass tube that contains a proprietary mixture of inert gases. The high voltage excites the gases in the tube into plasma and creates a lighted beam. The oscillator frequency matches the frequency of healthy human bioelectric fields. This beam is applied directly to the skin of the affected area of the subject by rubbing the glass tube in a back and forth or circular motion for a 15 minute interval. A feedback circuit maintains the frequency of the signal via capacitive sensing that automatically adjusts the output to match the load of each individual subject. The intensity or magnitude of the signal can be adjusted up or down manually by the operator via controls on the front panel of the unit. A user typically selects lower levels to treat sensitive areas such as the face and higher levels would be preferable to penetrate large muscles such as shoulder, back, and legs.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DETAILED DESCRIPTION

Figure 1:
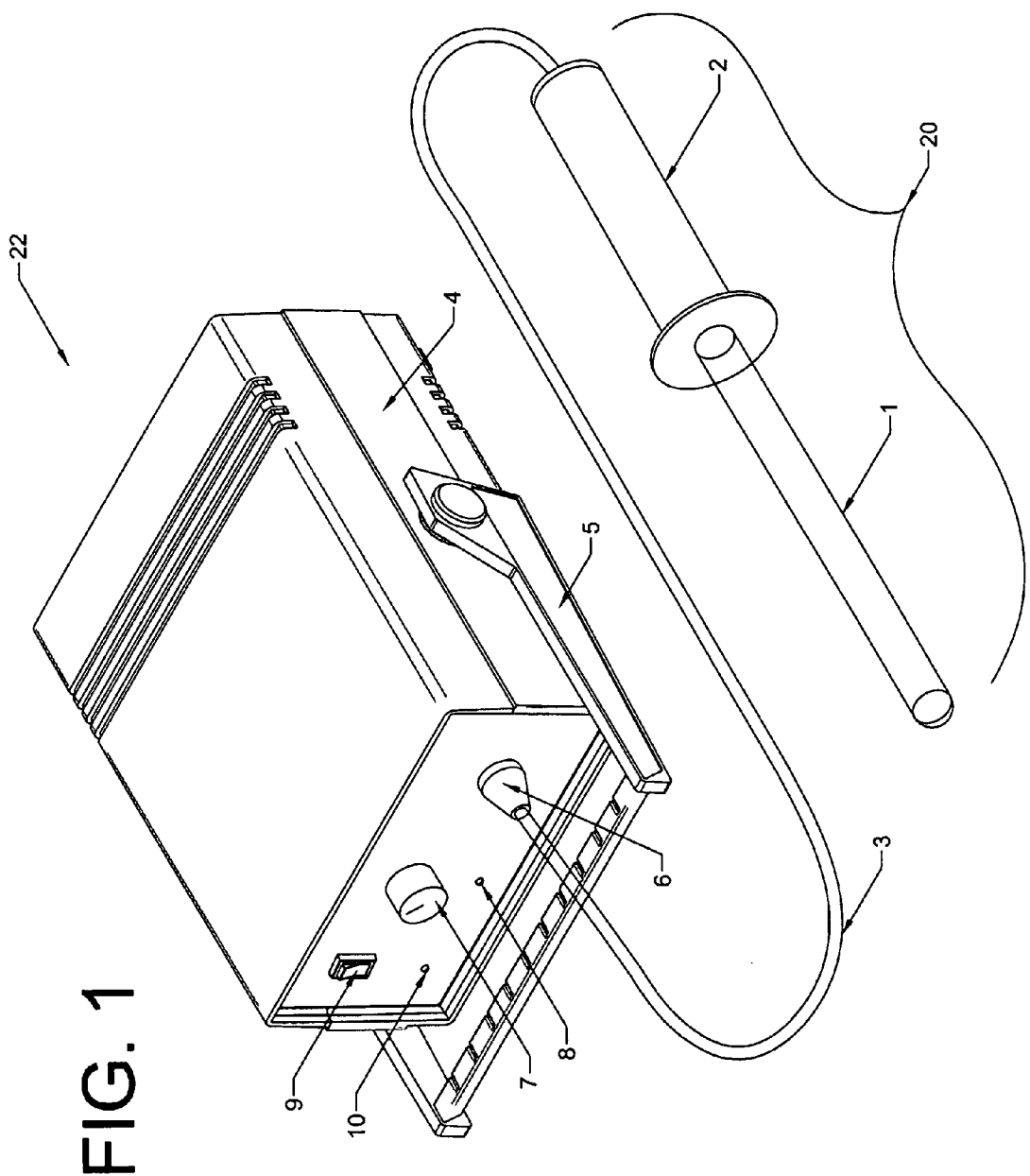
FIG. 1 is a perspective view of an electronic enclosure having a wand attached to the enclosure's output.
Figure 3:
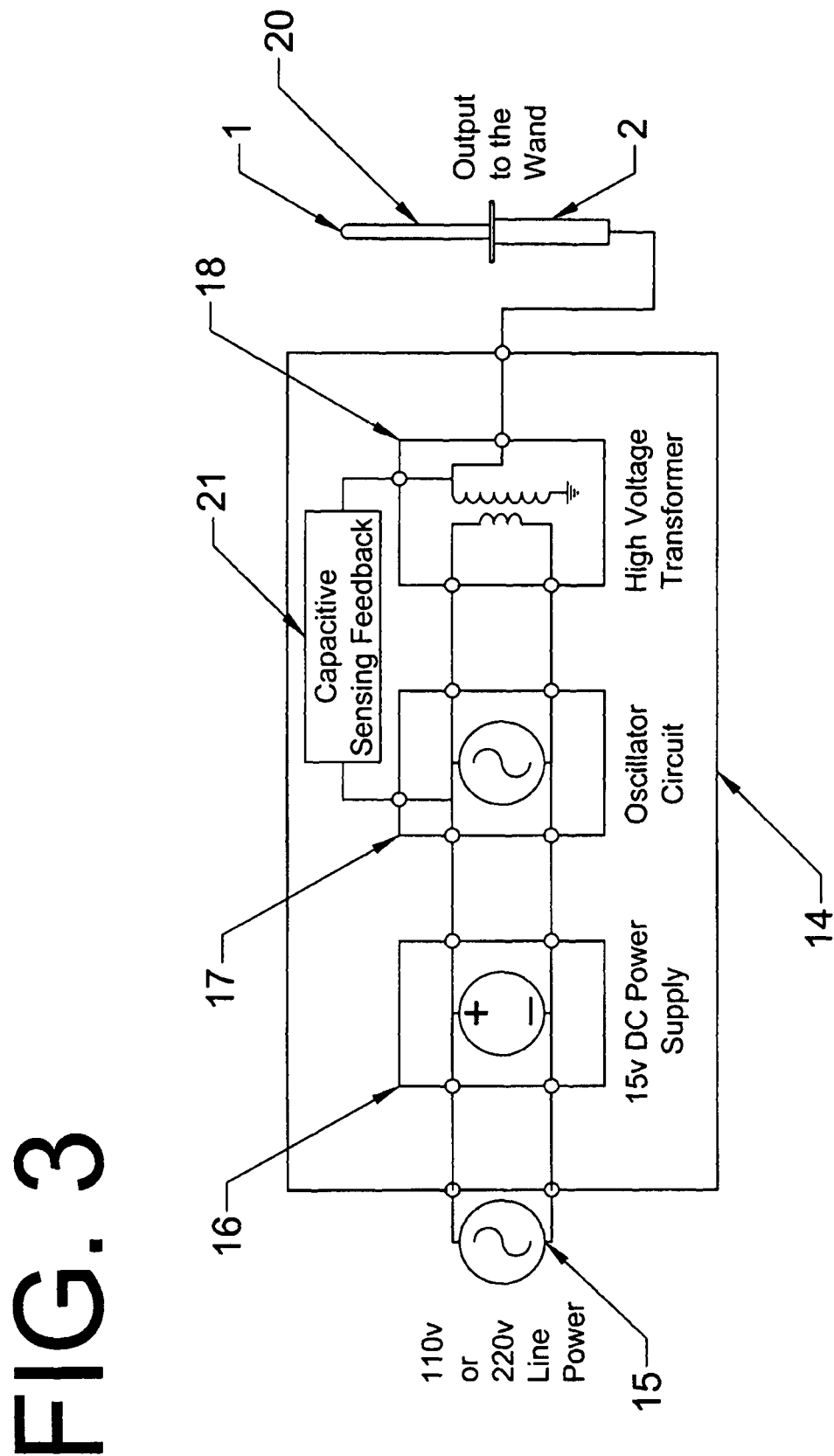
FIG. 3 is a schematic view of the main circuit for generating the output.

FIG. 1 shows a perspective view of the invention in its assembled state. In a preferred embodiment, the apparatus consists of a portable 11"×9"×4" electronics enclosure 4 containing various electronic components represented in FIG. 3. The portable unit weighs approximately sixteen (16) pounds and can be carried or elevated by the handle/stand 5. It is to be appreciated by someone skilled in the art that enclosure 4 can be other dimensions without departing from the spirit of the invention. A primary purpose of enclosure 4 is to house the electronic components required to operate the glass tube 1. Located on the front of enclosure 4 is connector 6 for connecting wand 20 to the output of the internal electronics. Wand 20 consists of glass tube 1 and handle 2. Wire 3 connects glass tube 1 to connector 6 to deliver power to glass tube 1. Output adjustment 7 adjusts the output power of the internal electronics delivered to glass tube 1. Main power indicator 8 indicates when the unit is energized from the input power. RF output indicator 10 indicates when high voltage RF output energy is delivered to glass tube 1. Output switch 9 controls the application of output energy to glass tube 1.

Figure 2:
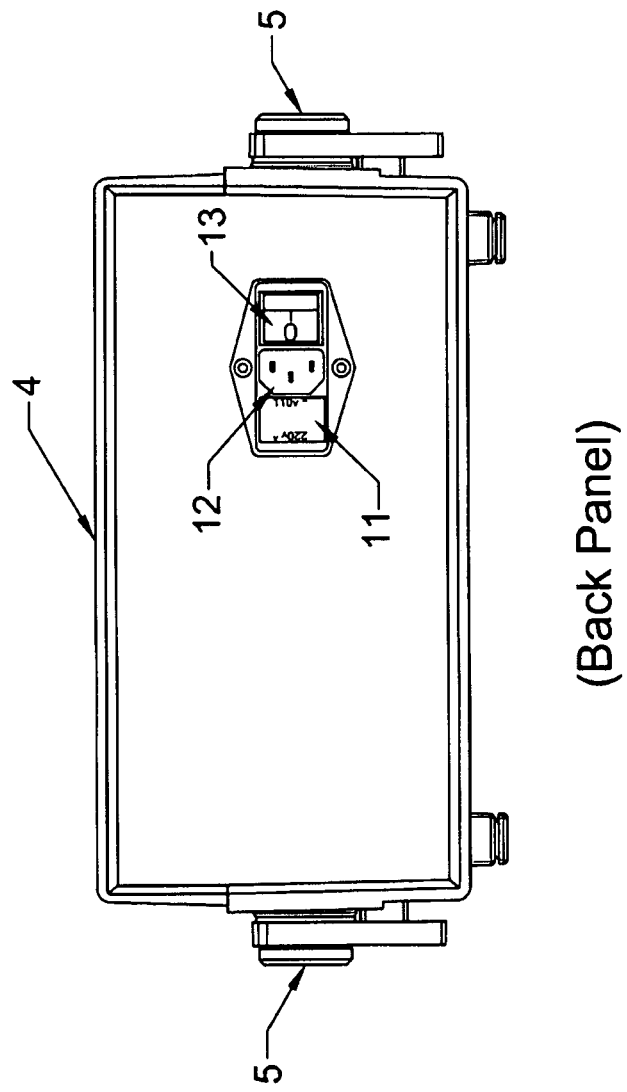
FIG. 2 is a rear view of the enclosure showing the power connector.

Referring now to FIG. 2, a rear view of enclosure 4 is shown. Located on the rear panel of enclosure 4 are voltage selector switch 11, main power connector 12, and main switch 13. The device operates on either 110 or 220 volt wall power 15 (see FIG. 3). In a preferred embodiment, a standard IEC wall power cord (not shown) is attached to the rear panel power connector 12 to supply power to the unit. Voltage selector switch 11 allows the unit to be configured to operate using either 110V or 220V.

When the Main power supply switch is moved to the "on" position, a cooling fan (not shown) will begin to run and the main power indicator 8 will be lit signifying that the unit is ready for use. Further, when the unit is energized, power is also applied to the DC power supply 16 (see FIG. 3). When the high voltage RF output switch 9 is turned on, the RF output indicator LED 10 will also light. This applies power from the 15-volt power supply 16 to the oscillator circuit 17, which delivers an output signal at RF frequency into the high voltage transformer 18, which outputs a high voltage RF signal. The high voltage RF output is sent via a 30 kV silicone wire 3 into a to insulated silicone handle 2 that houses an approximately 8" long by ¾" round glass tube 1 that contains a proprietary mixture of inert gases. The device has been used with tubes filled with Helium, Neon, Argon, Krypton and Xenon and each gas or mixture of gasses exhibits different healing characteristics. Certain generalizations have been noted of each of the different gasses that they specialize in the healing effects of specific conditions such as respiratory conditions, neurological disorders, and nerve regeneration however, more research needs to be conducted to confirm these findings. The preferred embodiment utilizes a proprietary mixture of inert gasses that have been found to exhibit the most universal healing effects of muscles and soft tissues. The high voltage RF signal excites the gas mixture into plasma, which in turn creates a lighted beam that emanates from glass tube 1. The glass tube 1 containing the beam is applied directly to dry bare skin in a rubbing motion on the affected area of the subject for a 15-minute interval. The frequency of the output signal is proprietary but falls within the audible spectrum. The frequency was chosen due to its non-reactive nature with salt and potassium ions in the human body, which conduct electricity and would produce an unpleasant sensation during treatments.

The oscillator circuit 17 is unique due to its self-tuning dubbed a "Self Resonant Circuit". Feedback circuit 21 senses the capacitive changes associated with the application of glass tube 1 to a patient's skin. Feedback circuit 21, unlike other devices of this type, utilizes the capacitive load of the biological entity that it is in contact with (i.e. human subject) to adjust its output so that it maintains the resonant frequency for the subject instead of drifting to another frequency. Capacitive load, or capacitive reactance, is an impedance to the flow of induced energy between the produced field and the body. Injuries such as cuts, hematomas, infections, bone breaks, etc. present distortions in a person's bio-field, which are recognized as capacitive reactance. The induced energy of the device is absorbed by the tissue initiating changes in the body at the location of the increased impedance. Since the capacitive load of each subject is different, most devices of this type cannot hold the proper harmonic resonance, which drastically reduces their efficacy. The device of the present invention senses the capacitive load of each subject and adjusts its output to maintain the proper resonant frequency dynamically during operation, thereby maintaining maximum efficacy during use.

The invention operates uniquely using four different healing mediums simultaneously.

1) The harmonic resonant frequency that the device uses was selected specifically for its ability to interface directly with the human bioelectric field. Research shows that the bioelectric field surrounding an injury is altered and depleted. The output from the Self Resonant Circuit mimics a healthy bio-rhythm which penetrates the tissue and replenishes the depleted field of the affected area which creates a natural healthy environment for the body to heal unobstructed. Research has shown this process holds its effectiveness in the treated tissues for a number of days before needing another treatment. Typical treatment intervals are a 15-minute treatment every 2-3 days with 4-6 treatments usually required for complete relief of the subject. However, different patients with differing injuries may require treatments of different duration and frequency.

2) The high voltage component of the device stimulates the tissue and relaxes constricted muscles, which, in turn, increases blood flow to accelerate the healing process. Recent Studies in Brazil have shown high voltage treatments have been effective in improving nerve regeneration in crush injuries. The high voltage also restores depleted zeta potential charge in the body's red blood cells back to a healthy state. Research has shown that this effect is a contributing factor to the commonly observed normalization of high blood pressure in treated subjects. Another effect of the high voltage is to raise the TMP of cells.

Figure 5:
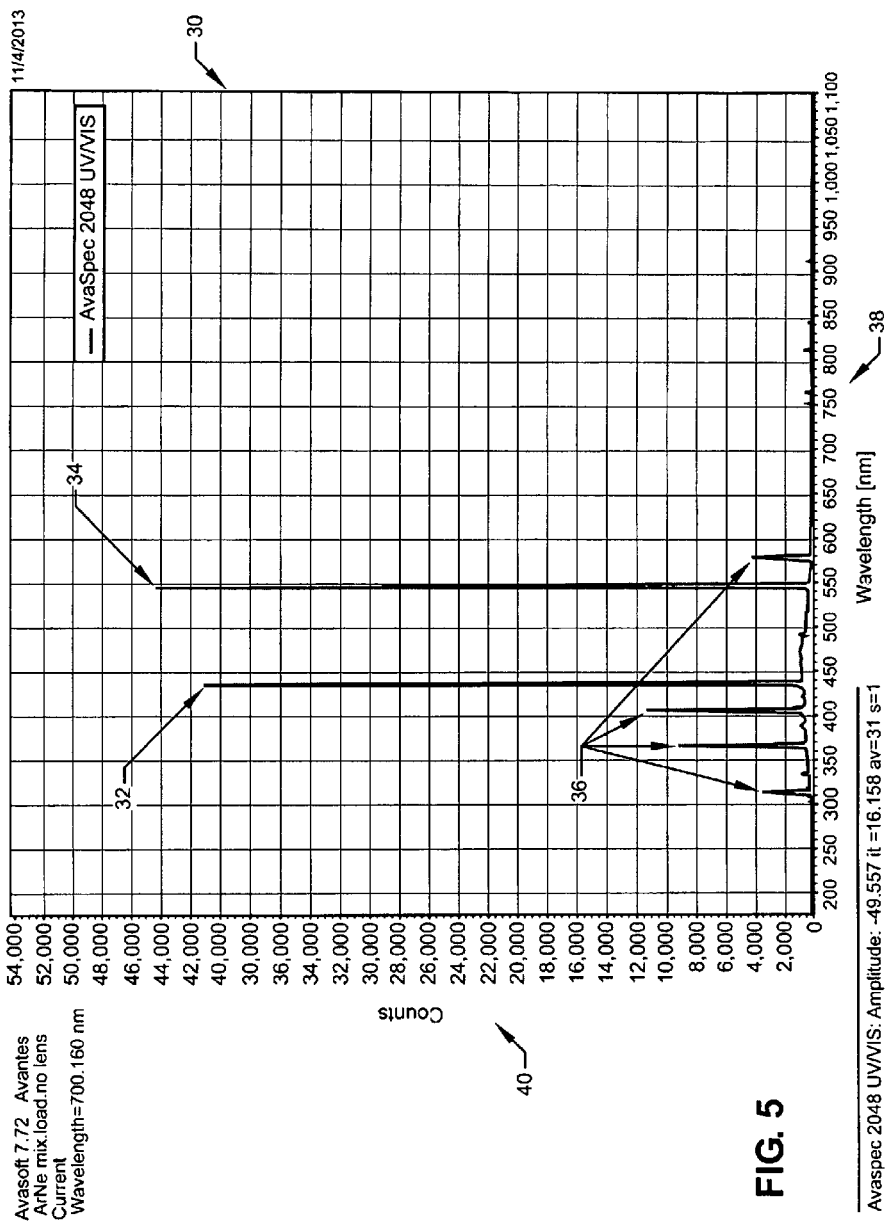
FIG. 5 is a chart showing the output wavelengths for a particular combination of gasses as read by a spectrometer.

3) The harmonic Radio Frequency is also coupled with a light output from glass tube 1 of a specific spectral signature (see FIG. 5). Different Inert gases or Inert gas mixtures each emit a different spectrum of light. Infrared and Ultraviolet light have been shown to have therapeutic effects on humans. Light therapy has limitations due to the ability of the light source to penetrate the tissue to a sufficient depth to treat the affected area. As light levels increase, exposure times must be reduced to minimize or eliminate any adverse effect on the surface skin. The present invention uses a unique combination of RF and light that is theorized to combine the therapy properties of light and the penetration properties of the Radio Frequency to increase the overall therapeutic effect.

4) The device produces ozone on the surface of the treated skin and effectively reduces superficial, as well as deeper tissue, infections. Ozone has been proven effective in killing bacteria, viruses, fungi, yeast, and protozoa as well as increasing stimulation of oxygen metabolism and activation of the immune system. Ozone therapy causes an increase in the red blood cell glycolysis rate thereby increasing ATP production, which is the energy source of all cells. This leads to the stimulation of 2,3-diphosphoglycerate, which leads to an increase in the amount of oxygen released to the tissues.

During testing of the present invention, the following benefits were noted: Significant reduction/normalization of high blood pressure, accelerated healing of recent superficial tissue damage, healing of old tissue damage, increased local circulation, acceleration of immune reactions, improved breathing, relief of frozen joints/tendons/ligaments, relief of muscle cramps & sprains, reduced arthritis symptoms, reduced healing time for bruises, reduce or eliminate headaches, minimizing chronic pain, reduce cellulite and wrinkles, increase healing rate of damaged tissue, and minimize pain and scarring from burns and abrasions.

Figure 4:
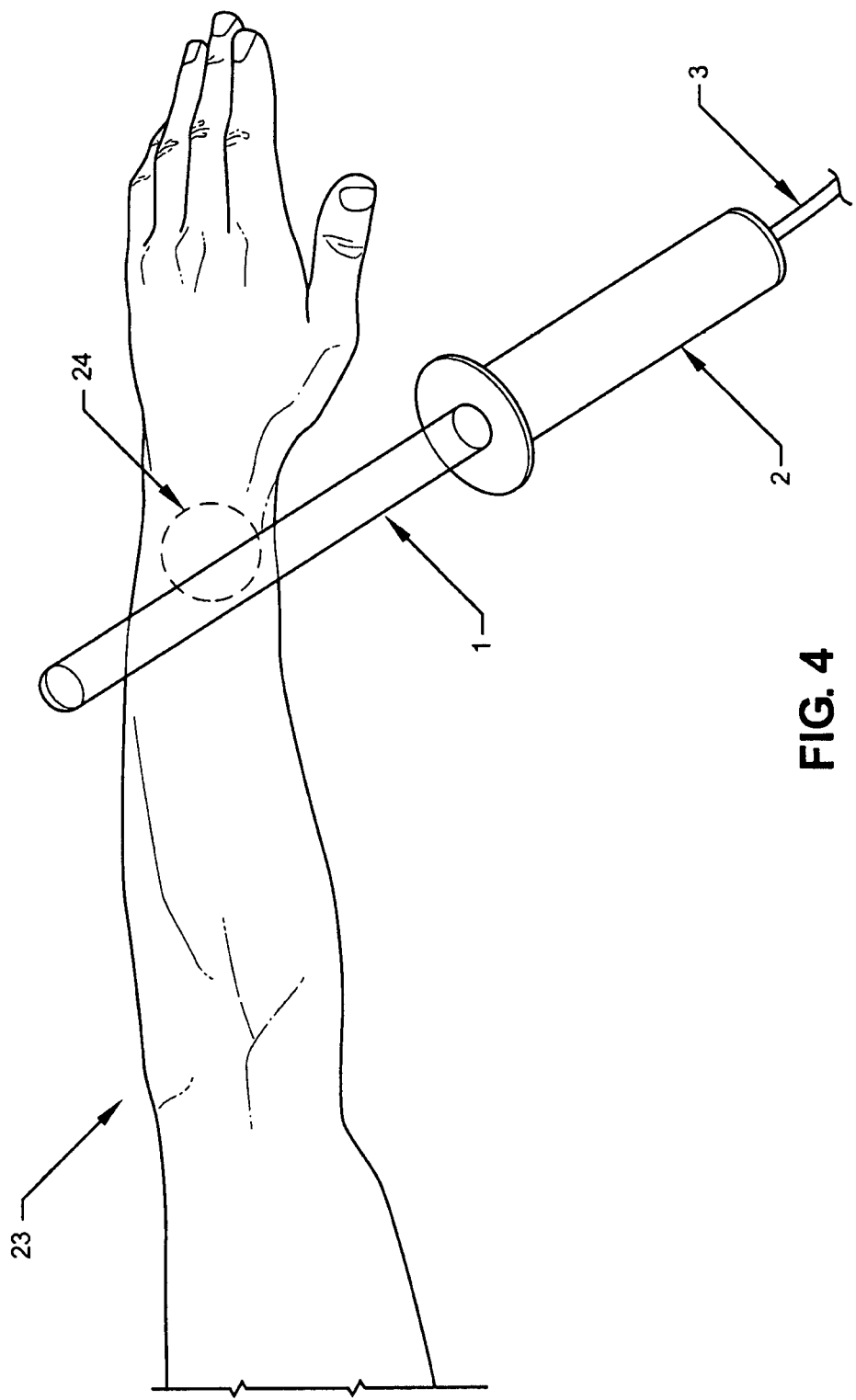
FIG. 4 is a perspective view of the wand of the present invention being used on a patients forearm.

Referring now to FIG. 4, a perspective view of the device of the present invention applied to a patient's skin is shown. In use, after system 22 is energized and output switch 9 is set to energize glass tube 1, glass tube 1 emits a plasma beam having an RF frequency component. A user then applies Glass tube 1 to a wound 24 located on a patient's body then slowly moved in a circular motion for approximately 15 minutes. There is a diagnostic property unique to the present invention where the previously mentioned reduced bio-field of the injured area will be positively charged and glass tube 1 having a negative charge will be statically attracted to each other and cause glass tube 1 to "stick" at the injury site. As the reduced bio-field is replenished from treating the affected area, glass tube 1 will no longer "stick". This allows to operator to determine the specific area to be treated and also when the area has received treatment for the proper duration. This procedure is repeated every 2-3 days until the patient receives permanent relief. It is to be appreciated by someone skilled in the art that the intensity and frequency of the output from glass tube 1 may vary necessitating the need to adjust the treatment duration and frequency of treatments.

Lastly, referring to FIG. 5, a chart illustrating the output wavelengths for a particular combination of gasses is shown and referred to as 30. The data represented in the chart was captured by a spectrometer using an ultraviolet/visible grating having a usable range of 250-850 nm. The independent variable in chart 30 is wavelength 38 and the dependent variable is Counts 40. The data shown in chart 30 is for a mixture of Argon and Neon gasses. This combination of gasses, when subjected to an oscillating voltage, generates several wavelengths of light. For this combination of gasses, the output has two (2) major peaks: 440 nm 32 and 550 nm 34. Below the 440 nm 32 peak are several smaller harmonic peaks 36 and above the 550 nm 34 peak is one smaller harmonic peak 36. As can be seen from chart 30, the output at the 440 nm 32 peak is approximately 41,000 counts while the output at the 550 nm 34 is approximately 44,000 counts. The harmonics 36 are in the range of 3,500-11,999 counts. It is to be appreciated by someone skilled in the art that various mixtures of different gasses produce different outputs. For instance, a mixture of Krypton and Xenon may produce an output consisting of three (3) or more peaks where the use of one gas may produce a single peak.

While there have been shown what are presently considered to be preferred embodiments of the present invention, it will be apparent to those skilled in the art that various changes and modifications can be made herein without departing from the scope and spirit of the invention.

I claim:

1. A medical biometric plasma beam generator, comprising:
   an enclosure containing a high voltage Radio Frequency oscillator circuit having an output and providing an electrical signal having a frequency and amplitude;
   a wand comprising a cylinder shaped glass tube containing at least one inert gas;
   an electrical connection between said wand and said output of said Radio Frequency oscillator circuit;
   a capacitive sensing feedback circuit configured to capacitively couple with a biological subject and automatically adjust said frequency of said electrical signal; and
   a control in electrical connection with said Radio Frequency oscillator circuit to adjust the amplitude of said electrical signal.

2. The medical biometric plasma beam generator as recited in claim 1, wherein said frequency of said Radio Frequency oscillator circuit is within the audible spectrum.

3. The medical biometric plasma beam generator as recited in claim 1, wherein said electrical connection between said wand and said output of said Radio Frequency oscillator circuit comprises a high voltage transformer having an input connected to said Radio Frequency oscillator circuit and an output.

4. The medical biometric plasma beam generator as recited in claim 3, wherein said electrical connection between said wand and said output of said Radio Frequency oscillator circuit further comprises a silicone wire connecting said output of said high voltage transformer to said wand.

5. The medical biometric plasma beam generator as recited in claim 3, wherein said capacitive sensing feedback circuit is in electrical connection with said Radio Frequency oscillator circuit and with said output of said high voltage transformer.

6. The medical biometric plasma beam generator as recited in claim 1, wherein said at least one inert gas comprises a mixture of inert gases.

7. A medical biometric plasma beam system comprising:
   a medical biometric plasma beam generator comprising an enclosure containing a high voltage Radio Frequency oscillator circuit having an output and providing an electrical signal having a frequency and amplitude;
   a wand comprising a cylinder shaped glass tube containing at least one inert gas;
   an electrical connection between said wand and said output of said Radio Frequency oscillator circuit;
   said wand configured to capacitively couple a biological subject having a capacitive load and a resonant frequency to said medical biometric plasma beam generator.

8. The medical biometric plasma beam system of claim 7 further comprising a capacitive feedback circuit configured to adjust said frequency of said Radio Frequency oscillator circuit based on said capacitive load of said biological subject.

9. The medical biometric plasma beam system of claim 8, wherein said capacitive feedback circuit maintains said frequency of said Radio Frequency oscillator circuit at said resonant frequency of said biological subject.

10. The medical biometric plasma beam system of claim 7, wherein said at least one inert gas comprises a mixture of inert gases.

11. The medical biometric plasma beam system of claim 10, wherein said plasma beam generator delivers several wavelengths of light to said biological subject.

12. The medical biometric plasma beam system of claim 7, wherein said wand comprises a negative charge.

13. The medical biometric plasma beam system of claim 12, wherein said biological subject comprises a positively charged area, wherein said wand is attracted to said positively charged area of said biological subject.

14. The medical biometric plasma beam system as recited in claim 7, wherein said electrical connection between said wand and said output of said Radio Frequency oscillator circuit comprises a high voltage transformer having an input connected to said Radio Frequency oscillator circuit and an output.

15. The medical biometric plasma beam system as recited in claim 7, wherein said medical biometric plasma beam generator is configured to produce ozone on said biological subject.

16. The medical biometric plasma beam generator as recited in claim 7, wherein said biological subject further comprises a plurality of cells comprising a zeta potential and a transmembrane potential, and wherein said medical biometric plasma beam generator is configured to increase said zeta potential and said transmembrane potential of said plurality of cells.

* * * * *